United States Patent [19]

Chung et al.

[11] Patent Number: 5,382,705

[45] Date of Patent: Jan. 17, 1995

[54] PRODUCTION OF TERTIARY ALKYL ETHERS AND TERTIARY ALKYL ALCOHOLS

[75] Inventors: Harold S. Chung, Princeton; Andrew Jackson, Pennington; Margaret M. Wu, Skillman, all of N.J.

[73] Assignee: Mobil Oil Corporation, Fairfax, Va.

[21] Appl. No.: 973,888

[22] Filed: Nov. 10, 1992

Related U.S. Application Data

[63] Continuation-in-part of Ser. No. 769,510, Oct. 1, 1991, abandoned, which is a continuation of Ser. No. 644,698, Jan. 22, 1991, abandoned, which is a continuation of Ser. No. 325,742, Mar. 20, 1989, abandoned.

[51] Int. Cl.$^6$ .............................................. C07C 41/06
[52] U.S. Cl. .................................... 568/697; 585/310; 568/895
[58] Field of Search ........................................ 568/697

[56] References Cited

U.S. PATENT DOCUMENTS

| 4,404,409 | 9/1983 | Fujiwara et al. | 568/697 |
|---|---|---|---|
| 4,542,199 | 9/1985 | Kaminsky | 526/160 |
| 4,571,439 | 2/1986 | Keyworth | 568/697 |
| 4,575,566 | 3/1986 | Vora | 568/697 |
| 4,658,078 | 4/1987 | Slaugh et al. | 585/512 |
| 4,740,631 | 4/1988 | Nagji et al. | 568/697 |
| 4,752,597 | 6/1988 | Turner | 502/104 |
| 4,788,365 | 11/1988 | Narandi et al. | 568/697 |
| 4,827,064 | 5/1989 | Wu | 585/10 |
| 4,827,073 | 5/1989 | Wu | 585/530 |
| 4,990,709 | 2/1991 | Wu | 585/10 |
| 5,171,331 | 12/1992 | Debras et al. | 568/697 |

*Primary Examiner*—Howard T. Mars
*Attorney, Agent, or Firm*—A. J. McKillop; M. D. Keen

[57] ABSTRACT

A process for upgrading a light olefin feed by converting the 1-olefins to higher molecular weight oligomers and the iso-oleins to fuel ethers or alcohols. The process provides substantial improvements in the production of lower alkyl tertiary alkyl ethers or tertiary alkyl alcohol, such as methyl tertiary butyl ether (MTBE), methyl tertiary amyl ether (TAME) or tertiary butyl alcohol. The 1-olefin component of the hydrocarbon feedstream is separated by selective oligomerization in contact with a reduced chromium oxide catalyst to form an olefin oligomer of higher molecular weight, such as gasoline, distillate and lube range hydrocarbons. The iso-olefins are separated by etherification with a lower alcohol such as methanol or by hydration to form an alcohol such as tertiary butanol. The oligomerization process can be integrated either upstream or downstream of the etherification step.

10 Claims, 3 Drawing Sheets

PRODUCTION OF TERTIARY ALKYL ETHERS AND TERTIARY ALKYL ALCOHOLS

CROSS-REFERENCE TO RELATED APPLICATIONS

This application is a continuation-in-part of our prior application Ser. No. 07/769,510, filed Oct. 1, 1991, which is a continuation of Ser. No. 07/644,698, filed Jan. 22, 1991, which was a continuation of Ser. No. 07/325,742, filed Mar. 20, 1989 all now abandoned.

FIELD OF THE INVENTION

This invention relates to an integrated process for upgrading $C_4$ olefin streams which are produced in a petroleum refinery. The process enables the straight chain $C_4$ 1-olefins to be efficiently and effectively separated from the corresponding branched-chain and straight chain internal olefins in an integrated process which converts both the 1-olefins and the branched-chain olefins to useful products. In this process, the branched-chain butenes are converted to tertiary ethers or alcohols and the straight chain 1-butenes to olefin oligomers which are useful as high quality lubricant stocks.

BACKGROUND OF THE INVENTION

In recent years, a major technical challenge presented to the petroleum refining industry has been the requirement to establish alternative processes for manufacturing high octane lead-free gasoline which produces lower levels of airborne pollutants. The economic impact of these requirements on the cost of gasoline is significant and workers in the field have intensified their effort to develop new processes to manufacture environmentally acceptable gasoline products. One approach which has been taken in view of the regulatory requirement for oxygenates in the gasoline is the use of gasolines blended with lower aliphatic alkyl ethers such as methyl-tertiary butyl ether (MTBE) or methyl tertiary amyl ether (TAME) as octane boosters and supplementary fuel components. Ethers of this type, especially the $C_5$–$C_7$ methyl alkyl ethers, especially tertiary alkyl ethers such as methyl tertiary butyl ether (MTBE) and tertiary amyl methyl ether (TAME), or the corresponding tertiary alcohol, have been found particularly useful for enhancing gasoline octane.

MTBE and TAME are known to be high octane ethers. The article by J. D. Chase, et al., *Oil and Gas Journal*, Apr. 9, 1979, discusses the advantages one can achieve by using these materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

Isobutylene may be reacted with methanol over an acidic catalyst to provide methyl tertiary butyl ether (MTBE) and isoamylenes may be reacted with methanol over an acidic catalyst to produce tertiary-amyl methyl ether (TAME). Similarly, these iso-olefins can be hydrated in the presence of an acid catalyst to give alcohols. In these processes, a problem of major importance is the separation of the reaction products and separation of unreacted hydrocarbons. For instance, the feedstream to an etherification process can be the $C_4$ and/or $C_5$ fraction from a fluid catalytic cracking (FCC) unit containing a range of isomeric alkanes and alkenes; of these, only the iso-olefins react with the alcohol (methanol or ethanol) to form the tertiary butyl or tertiary amyl ether.

Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, to which reference is made for a description of such processes. Olefin hydration processes employing zeolite catalysts are disclosed, for example, in U.S. Pat. No. 4,214,107, to which reference is also made. In this process, lower olefins, particularly propylene, are catalytically hydrated over a crystalline aluminosilicate zeolite catalyst having a silica to alumina ratio of at least 12 and a Constraint Index of from 1 to 12, e.g., HZSM-5 zeolite, to provide the corresponding alcohol, essentially free of ether and hydrocarbon by-product.

Recently, synthetic lubricant compositions (referred to here as HVI-PAO lubricants) comprising high viscosity index polyalpha-olefins and methods for their preparation using a reduced chromium oxide catalyst have been disclosed in U.S. Pat. Nos. 4,827,064 and 4,827,073, to which reference is made for a description of thse olefin oligomers, their preparation and properties. The process described in these patents comprises contacting a $C_6$–$C_{20}$ 1-olefin feedstock with a reduced chromium oxide catalyst on a porous silica support under oligomerizing conditions to produce a high viscosity, high VI liquid hydrocarbon lubricant. The product is characterized by a branch ratio less than 0.19 and low pour point, typically below $-15°$ C. The process is notable in that internal or iso-olefins are unreactive in the oligomerization; only terminal olefinic groups participate in the coordination catalyzed oligomerization using the reduced chromium oxide catalyst. The same process may also be applied to the production of high VI lubricants from lower olefins, such as propylene and butene, as described in U.S. Pat. No. 4,990,709, to which reference is made for a description of the process using these olefins and of the oligomer products.

SUMMARY OF THE INVENTION

We have now devised a process which is capable of converting mixed olefin streams containing both straight and branched-chain olefins to useful products including lower alkanol tertiary alkyl ethers, particularly MTBE, or secondary or tertiary alkyl alcohols, as well as high viscosity index lubricant products. The integrated process enables the 1-olefins to be separated from the branched olefins and oligomerized to form the desired lubricants. The branched chain olefins are converted to ethers or alcohols which are useful as fuel components. Substantial improvements in the production of the lower alkyl tertiary alkyl ethers, e.g. MTBE and TAME or the corresponding tertiary alcohols, are realized when the 1-alkene component of the hydrocarbon feedstream to an etherification or olefin hydration process is separated by selective oligomerization in contact with the reduced chromium catalyst. Conversely, the production of the high viscosity index oligomers is enhanced by the use of the olefin feedstream containing the essentially unreactive branched-chain olefins. The quality of the product is also improved in this way. The 1-olefin component of the hydrocarbon feedstream can be separated in an oligomerization process integrated either upstream or downstream of the etherification or hydration step.

In its first form, the integrated process for the production of oxygenates comprising lower alkyl tertiary alkyl ethers and tertiary alkyl alcohols and higher molecular weight olefins from $C_4+$ olefins comprises:

a) contacting a lower alkanol or water feedstream and a $C_4+$ hydrocarbon feedstream containing both iso-olefins and 1-olefins with an acid catalyst under etherification or hydration conditions to form an effluent stream comprising lower alkyl tertiary alkyl ethers or tertiary alkyl alcohols and unreacted $C_4+$ hydrocarbons containing 1-alkene components;

b) separating the effluent stream to recover the ether or tertiary alcohol component;

c) passing 1-olefins to an oligomerization step in which the 1-olefins are oligomerized in the presence of a reduced chromium oxide catalyst to form higher molecular weight olefin oligomers.

In the alternative from, in which the oligomerization precedes the etherification or hydration, the process comprises:

a) contacting a feed stream comprising the $C_4+$ olefins with a reduced chromium oxide on silica support catalyst under oligomerization conditions so that the 1-olefin component of the feedstream is oligomerized to produce an effluent stream containing higher molecular weight olefin oligomer and unreacted $C_4+$ iso-olefins;

b) separating and recovering the higher molecular weight olefin oligomer;

c) passing the unreacted olefins and a lower alkanol feedstream to an etherification or hydration zone in which the iso-olefins are subjected to etherification or hydration in the presence of an acidic catalyst to produce effluent stream containing lower tertiary alkyl ethers or alcohols.

DRAWINGS

DETAILED DESCRIPTION

In the present process, oxygenates—lower tertiary alkyl ethers or alcohols—and higher molecular weight olefins are produced from the same feedstream. The oxygenates are produced by either etherification or hydration of the branched-chain iso-olefins while the higher molecular weight olefin oligomers are produced by oligomerization of the 1-olefins which are present in the feed. The term "oxygenates" or "oxygenate" used here refers to $C_1$-$C_8$ lower aliphatic, acyclic alcohols or alkanol and symmetrical or unsymmetrical $C_2$-$C_9$ethers.

The present invention utilizes the capability of the HVI-PAO oligomerization process using the reduced metal oxide catalysts to selectively oligomerize 1-alkenes without oligomerizing the alkenes containing only internal olefin bonds. The process can therefore be used to convert 1-alkenes in a mixture of hydrocarbons containing other unsaturated olefinic isomers and alkanes to produce higher polymers of the 1-alkenes (polyalpha-olefins), in the form of valuable higher molecular weight products. These oligomers with olefinic unsaturation can be used as starting material for detergents, additives and many other chemicals. Following hydrogenation by conventional processes, they also can yield useful gasoline, distillate and lube range products. When this capability of the HVI-PAO oligomerization process is integrated with the iso-olefin etherification or olefin hydration processes using mixed hydrocarbon feedstocks containing 1-alkenes, the 1-alkene is separated, enhancing the performance of the etherification or hydration processes, such as MTBE or tertiary butyl alcohol (TBA) production.

Olefins suitable for use as starting material in the process include olefins such as those from an FCC unsaturated gas plant containing from 2 to about 20 carbon atoms such as ethylene, propylene, butene, pentene and hexene and branched chain isomers such as iso-butene, iso-pentene and 4-methyl-1-pentene. Also suitable for use are refinery olefinic hydrocarbon feedstocks or effluents containing alpha olefins. Typically, such feedstock will also be rich in $C_4+$ iso-olefins and other olefin isomers and generally is comprised of 1-butene, 2-butene, isobutene, 1-pentene, 2-pentene and isoamylene and higher hydrocarbons.

Figure 1:
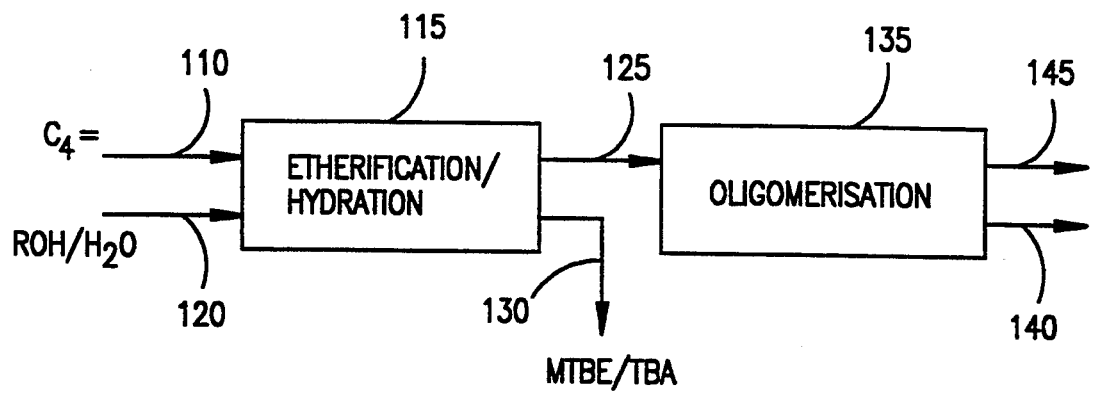
FIG. 1 is a block diagram process schematic showing the process in which oligomerization takes place downstream of the etherification.

FIG. 1 shows the form of the process in which the HVI-PAO process is downstream of the etherification process producing MTBE or a hydration process producing TBA. A $C_4$ or $C_4+$ stream 110 containing 1-alkene and iso-butene is passed to an etherification or hydration zone 115 together with methanol or water feedstream 120. The etherification or hydration effluent is separated to provide a raffinate stream 125 containing hydrocarbons including 1-alkene while MTBE is recovered in stream 130 in the case of etherification and TBA is recovered in the case of hydration. The raffinate stream 125 is passed to HVI-PAO process oligomerization zone 135 wherein 1-alkene hydrocarbons are selectively converted to higher molecular olefins and, in particular, poly-1-butene liquids. The effluent from the oligomerization zone is separated to recover oligomeric olefins 140 including poly-1-butene and a stream 145 containing unreacted $C_4$ or $C_4+$ hydrocarbons.

The raffinate stream from MTBE or other etherification units, containing 1-, 2-butenes and/or butanes, is reacted over $Cr/SiO_2$ type catalysts to give useful liquid products. The residual $C_4$ stream, rich in 2-butene and/or butanes, can be used in alkylation units, or starting material for butadiene or isomerization reactor to upgrade 2-butene into mixed butenes.

Figure 2:
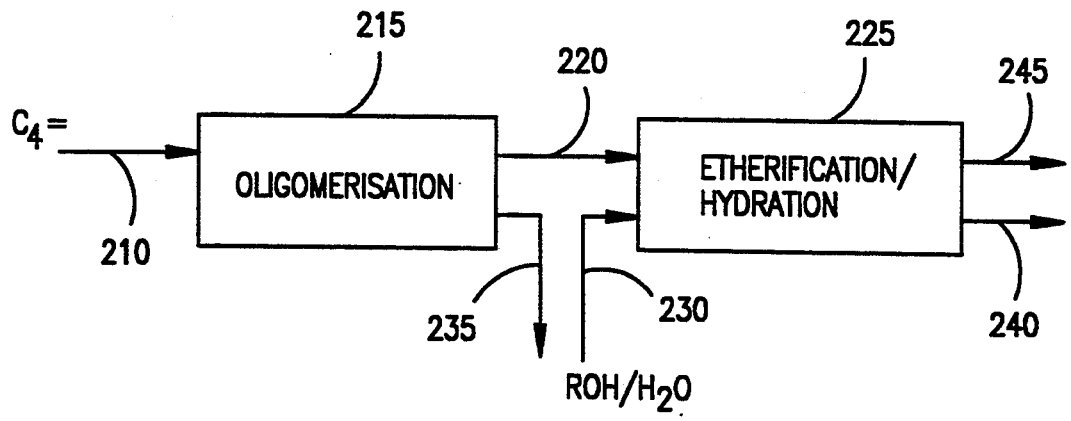
FIG. 2 is a block diagram process schematic showing the process in which the oligomerization takes place upstream of the etherification.

FIG. 2 shows the alternative form of the process in which the HVI-PAO process is integrated upstream of etherification or hydration unit. In this embodiment the $C_4$ or $C_4+$ feedstream 210 containing 1-alkene and iso-olefins is passed to the oligomerization zone 215. The effluent is separated and a raffinate stream 220 containing unreacted iso-olefins is passed to etherification or hydration zone 225 in conjunction with methanol or water feedstream 230 while oligomerization product is recovered in stream 235. The effluent from the etherification or hydration zone is separated to provide MTBE or TBA 240 and unreacted hydrocarbons, 245.

Here, the mixed $C_4$ stream is first reacted over an $Cr/SiO_2$ type catalyst to selectively remove 1-butene. The raffinate is then fed into a MTBE or etherification unit to remove i-butene. The residual stream is rich in 2-butene and/or butanes.

In both embodiments, the 1-butene is selectively removed and converted into useful liquid products over a Cr/SiO$_2$ catalyst. The residual 2-butene streams, usually of little use and low value, can be isomerized into higher-value 1- or iso-butenes, can be used in alkylation units or dehydrogenated into butadiene. These operations separate 1- and 2-butenes without complicated distillation or sorption techniques.

In both embodiments the liquid oligomer product can be used as a starting material for additives, lubricants, gasoline or distillates, preferably after hydrotreating to remove any residual unsaturation.

1-Olefin Oligomerization

The 1-olefins are separated from the mixed olefin feedstream by oligomerization using the oligomerization process described in U.S. Pat. No. 4,990,709, to which reference is made for a description of the process. The process is operated in substantially the same way as the process using the higher olefins, described in U.S. Pat. Nos. 4,827,064 and 4,827,073, to which reference is also made for a detailed description of the process. The oligomerization catalyst and process are described briefly below.

The alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstroms are preferred.

The support material usually has high surface area and large pore volumes with average pore size of 40 to about 350 angstroms. The high surface area is beneficial for supporting large amounts of highly dispersive, active chromium metal centers and to give maximum efficiency of metal usage, resulting in very high activity catalyst. The support should have large average pore openings of at least 40 angstroms, with an average pore opening of |60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, H$_2$, NH$_3$, H$_2$S, CS$_2$, CH$_3$SCH$_3$, CH$_3$SSCH$_3$, metal alkyl containing compounds such as R$_3$Al, R$_3$B, R$_2$Mg, RLi, R$_2$Zn, where R is alkyl, alkoxy, aryl and the like. Preferred are CO or H$_2$ or metal alkyl containing compounds. Alternatively, the Group VIB metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° F. for a period of about 16 to 20 hours. Thereafter the catalyst is cooled down under an inert atmosphere to a temperature of about 250° to 450° C. and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally, the catalyst is cooled down to room temperature and is ready for use. The oligomerization process itself is typically carried out at a temperature of 90° to 250° C. or at temperatures below about 90° C. for higher molecular weight products.

Etherification and Hydration

A lower alcohol such as methanol, ethanol, 1-propanol or isopropanol, but preferably methanol, is reacted with the iso-olefin components of the C$_4$+ olefinic feed to produce tertiary ethers which are useful as fuel components, including methyl tertiary alkyl ethers, particularly methyl tertiary butyl ether and methyl tertiary amyl ether. Alternatively, the olefins may be hydrated by reaction with water to form the corresponding alcohol such as tertiary butyl alcohol, 2-butanol, 2-pentanol, 3-pentanol, 3-methyl , 2-butanol and the like.

In the etherification reaction, the alkanol, or lower alcohol such as methanol, is generally present in an excess amount between 2 wt. % to 100 wt %, based upon iso-olefins. Excess methanol means excess methanol above the stoichiometric equivalent amount to convert isoolefins in the hydrocarbon feedstream to methyl tertiary alkyl ethers. Following the etherification reaction, the etherification reaction effluent stream, which comprises unreacted methanol, hydrocarbons including a major portion of C$_4$+ hydrocarbons and methyl tertiary alkyl ethers, are separated according by fractionation or extraction.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites.

The reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149–152, discusses the technology. A preferred catalyst is a bifunctional ion exchange resin which etherifies and isomerizes the reactant streams. A typical acid catalyst is Amberlyst 15 sulfonic acid resin.

Processes for producing and recovering MTBE and other methyl tertiary alkyl ethers from $C_4$–$C_7$ isoolefins are known to those skilled in the art, such as disclosed in U.S. Pat. Nos. 4,544,776 (Osterburg, et al.) and 4,603,225 (Colaianne et al.). Various suitable extraction and distillation techniques are known for recovering ether and hydrocarbon streams from etherification effluent.

The production of tertiary alcohols of high octane number by hydration of olefins in contact with acidic catalyst, which is an alternative to the olefin etherification for the separation of the iso-olefins from the feedstream, is also a known process.

Examples 1 to 3 below illustrate the HVI-PAO olefin oligomerization process which is used to separate the 1-olefins from the feedstream.

EXAMPLE 1

Catalyst Preparation and Activation Procedure 1.9 grams of chromium (II) acetate ($Cr_2(OCOCH_3)_4 \cdot 2H_2O$) (5.58 mmole) (commercially obtained) is dissolved in 50 cc of hot acetic acid. Then 50 grams of a silica gel of 8–12 mesh size, a surface area of 300 $m^2/g$, and a pore volume of 1 cc/g, also is added. Most of the solution is absorbed by the silica gel. The final mixture is mixed for half an hour on a rotavap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (99.99% from Matheson) is introduced for one hour. Finally, the catalyst is cooled down to room temperature under $N_2$ and ready for use.

EXAMPLE 2

The catalyst prepared in Example 1 (3.2 g) is packed in a ⅜″ stainless steel tubular reactor inside a $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
| --- | --- | --- | --- | --- |
| T.O.S., hr. | 2 | 3.5 | 5.5 | 21.5 |
| Lube Yield, wt % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

EXAMPLE 3

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
| --- | --- | --- | --- | --- |
| T.O.S., hrs. | 3.5 | 4.5 | 6.5 | 22.5 |
| Lube Yield, % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr on a silica catalyst support are also effective for oligomerizing olefins and can be used in the process.

EXAMPLE 4

Eleven grams of 1-hexene and 10 g 2-hexenes are mixed with 1.5 g of an activated Cr on silica catalyst, prepared by calcining a catalyst containing 0.91% Cr and 2.12% Ti on silica at 600° C. with air followed by reduction with CO at 300° C. The reaction is traced by GC which data demonstrates that 1-hexene can be selectively reacted away in the presence of other hexenes. The contents of 2-hexenes remained constant throughout the reaction. 2-hexenes are unreactive.

EXAMPLE 5

A catalyst, 3 grams, containing 3 wt % Cr on silica gel, calcined at 600° C. with air for 16 hours and reduced with CO at 350° C. for one hour, is packed in a ⅜″ stainless steel tube reactor. 1-Butene is fed through the reactor at 160° C. 350 psi and WHSV of 2. After 21.5 hours reaction time 134 grams of liquid product is collected. The conversion of 1-butene to liquid was 100%. The liquid product was fractionated to give 3 fractions:

Fraction 1, boiling up to 140° C./atm, 15.3 wt %, mostly octenes;

Fraction 2, boiling up to 160° C./0.1mm Hg, 56%, mostly $C_{12}$ to $C_{24}$ olefins;

Fraction 3, residual, 28.7 wt %, with the following viscometric properties:

V@100° C.=28.65 cS, V@40° C.=411.37 cS, VI=96

EXAMPLE 6

Similar to Example 5, except reaction temperature is 123° C. The liquid yield from 1-butene is 100%. The liquid product is fractionated to give the following fractions:

Fraction 1, boiling up to 140° C./atm, 0.4 wt %.

Fraction 2, boiling up to 160° C./0.1 mm Hg, 23.6 wt %, mostly $C_{12}$ to $C_{24}$ olefins product yields and lube properties are set out in Table 1 below.

TABLE 1

Mixed Butene Reaction Over Cr/SiO2
Effect of Temperature

| Run No. | Feed | A | B | C | D | E | F |
|---|---|---|---|---|---|---|---|
| Temperature, C | — | 88 | 102 | 128 | 142 | 158 | 176 |
| WHSV, g/g/hr | — | 2 | 1.6 | 1 | 1 | 2 | 4 |
| TOS, hours | — | 46 | 44 | 5 | 16 | 22.5 | 16 |
| Liq. prod. comp. wt % | | | | | | | |
| C8 | — | 8.6 | 9.0 | 27.5 | 25.4 | 42.6 | 39.5 |
| C12 | — | 6.13 | 5.1 | 15.4 | 15.7 | 19.6 | 21.2 |
| C16 | — | 3.5 | 10.8 | 9. | 10.3 | 10.8 | 11.5 |
| C20 | — | 4.8 | 4.0 | 8.3 | 10 | 6.6 | 7.2 |
| C24 | — | 6.0 | 6.7 | 5.8 | 6.1 | 4.1 | 4.4 |
| C28 | — | 5.4 | 7.8 | 4.1 | 5.7 | 4.8 | 2.6 |
| C28+ | — | 66.0 | 56.6 | 29.2 | 26.9 | 11.5 | 13.5 |
| Gas prod. comp. wt % | | | | | | | |
| 1-C4 | 26.6 | 16.3 | 16.5 | 13.6 | 8.9 | 7.2 | 13.3 |
| i-C4 | 26.8 | 31.1 | 31.1 | 31.1 | 90.5 | 92.1 | 33 |
| trans-2-C4 | 25.1 | 27.9 | 27.9 | 28.4 | | | 27.6 |
| cis-2-C4 | 21.2 | 24.3 | 24.1 | 26.5 | | | 26.1 |
| Total C4 conv. wt % | — | 7 | 8 | 31 | 42 | 48 | 49 |
| Conversion of each individual butene, wt % | | | | | | | |
| 1-butene | — | 43 | 43 | 67 | 81 | 87 | 75 |
| i-butene | — | 0 | 0 | 18 | 28 | 51 | 44 |
| C,t-2-butene | — | 0 | 0 | 12 | | | 36 |
| Lube properties | | | | | | | |
| V@100C, cS | — | 67.19 | 25.72 | 10.99 | 7.38 | 8.12 | 11.68 |
| V@40C, cS | — | 1890.46 | 420.32 | 83.68 | 51.67 | 69.69 | 95.8 |
| VI | — | 86 | 80 | 118 | 103 | 79 | 110 |

Fraction 3, residual, 76 wt %, with the following viscometric properties
V@100° C.=70.13 cS, V@40° C.=1904.92 cS, VI=89.

EXAMPLE 7

A mixed butene stream containing 27% butene-1, 46% butene-2 and 27% iso-butene, was fed through a continuous, fixed-bed reactor packed with an activated Cr/SiO2 catalyst using the procedure described above in Example 2. The reaction conditions, conversions,

EXAMPLE 8

A mixed butene stream containing 38% butene-1 and 61% butene-2 was passed through an activated Cr/SiO2 catalyst. The reaction conditions, conversions, product yields and lube properties are set out in Table 2 below.

TABLE 2

1-Butene and 2-butene reaction over Cr/SiO2

| Run No. | Feed | G | H | I | J | K |
|---|---|---|---|---|---|---|
| Temperature, °C. | | 90 | 100 | 129 | 157 | 172 |
| WHSV, g/g/hr | — | 2 | 2 | 2 | 2 | 2 |
| TOS, hours | — | 22 | 70 | 95 | 120 | 142 |
| Liq. prod. compn. wt % | | | | | | |
| C8 | — | 4.8 | 3.5 | 15.4 | 27.3 | 29.9 |
| C12 | — | 4.4 | 3.7 | 11.6 | 15.9 | 17.7 |
| C16 | — | 3.6 | 3.1 | 8.1 | 10.2 | 10.3 |
| C20 | — | 3.8 | 3.7 | 8.2 | 8.9 | 8.7 |
| C24 | — | 3.2 | 3.1 | 6.9 | 5.6 | 5.5 |
| C28 | — | 3.5 | 3.5 | 6.6 | 6.3 | 5.4 |
| C28+ | — | 76.8 | 79.4 | 43.2 | 25.8 | 22.5 |
| Gas prod. compn. wt % | | | | | | |
| 1-C4 | 3.83 | 7.9 | 9.0 | 6.8 | 7.1 | 9.0 |
| i-C4 | 1.1 | 1.0 | — | — | — | — |
| cis-2-C4 | 33.2 | 47.3 | 47.6 | 45.3 | 36.4 | 33.1 |
| trans-2-C4 | 27.7 | 45.2 | 42.6 | 47.0 | 55.2 | 56.4 |
| Total C4 conv. % | — | 46 | 47 | 37 | 60.2 | 76.2 |
| Conversion of individual butene, wt % | | | | | | |
| 1-butene | — | 88.8 | 87.6 | 89 | 92.6 | 94.4 |
| i-butene | — | — | — | — | — | — |
| cis-2-butene | — | 22.6 | 24.5 | 14 | 56.3 | 76.4 |
| trans-2-butene | — | 11.3 | 17.1 | 7 | 20.7 | 51.7 |
| Lube properties | | | | | | |
| V@100C, cS | — | 110.87 | 72.3 | 83.4 | 23.45 | 21.6 |
| V@40C, cS | — | 4910.46 | 2246.66 | 3439.21 | 333.09 | 326.97 |
| VI | — | 80 | 83 | 71 | 88 | 77 |

Runs A and B of Table 1 show that only 1-butene is converted into oligomers while 2-butene and iso-butene were inert under these conditions. At higher temperatures, (Runs C–F), conversion of the 1-butene remained much higher than that of the 2-butene or iso-butene.

Runs G–K of Table 2 show that 88 to 94 percent of the 1-butene was converted into oligomers but only 7 to 76 percent of the 2-butene was reacted away, demonstrating the selective character of the oligomerization process as between the 1-olefins and the internal olefins.

Figure 3:
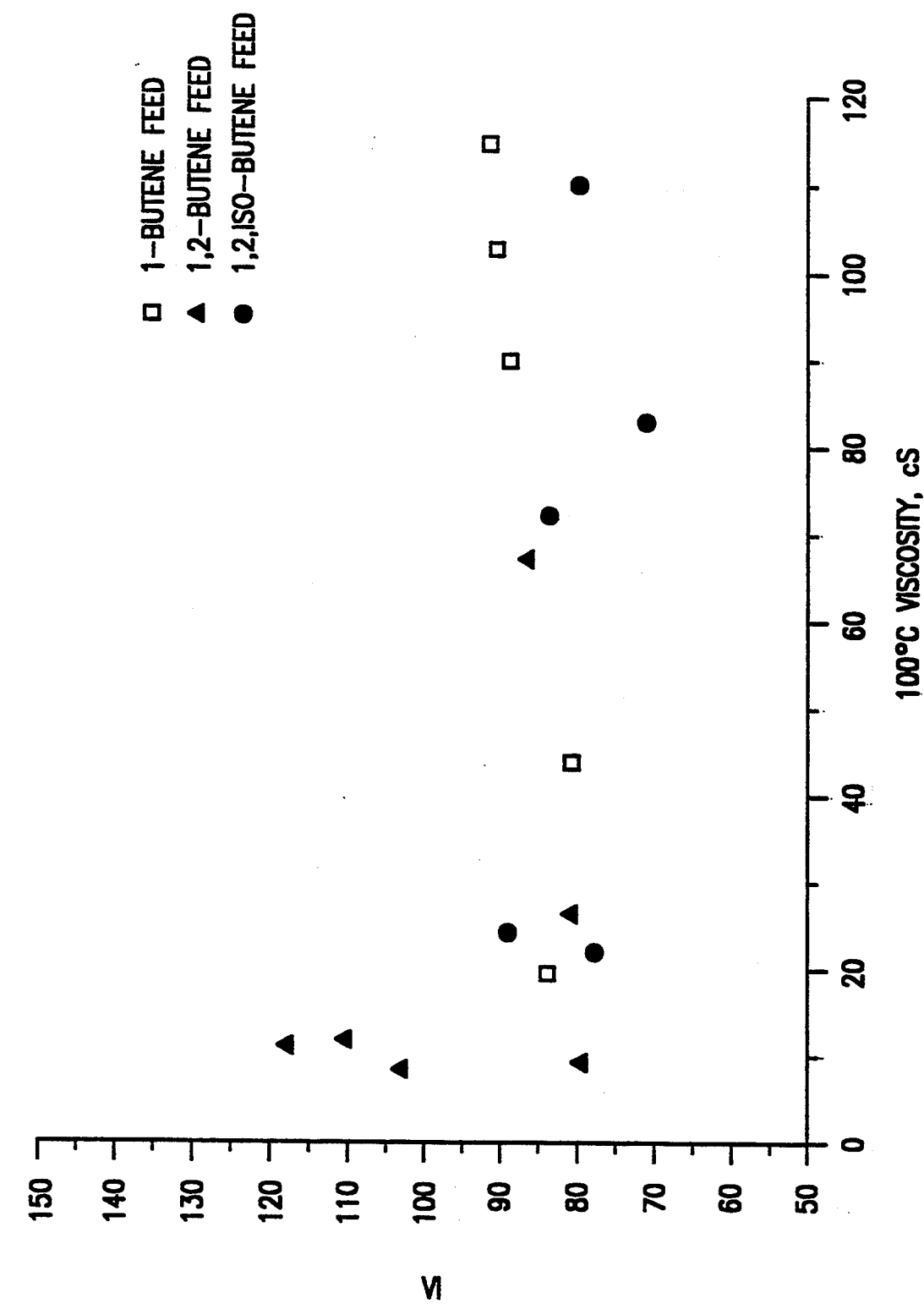
FIGS. 3 and 4 are graphs showing the effect of the oligomerization reaction conditions on the product characteristics, as described below.
Figure 4:
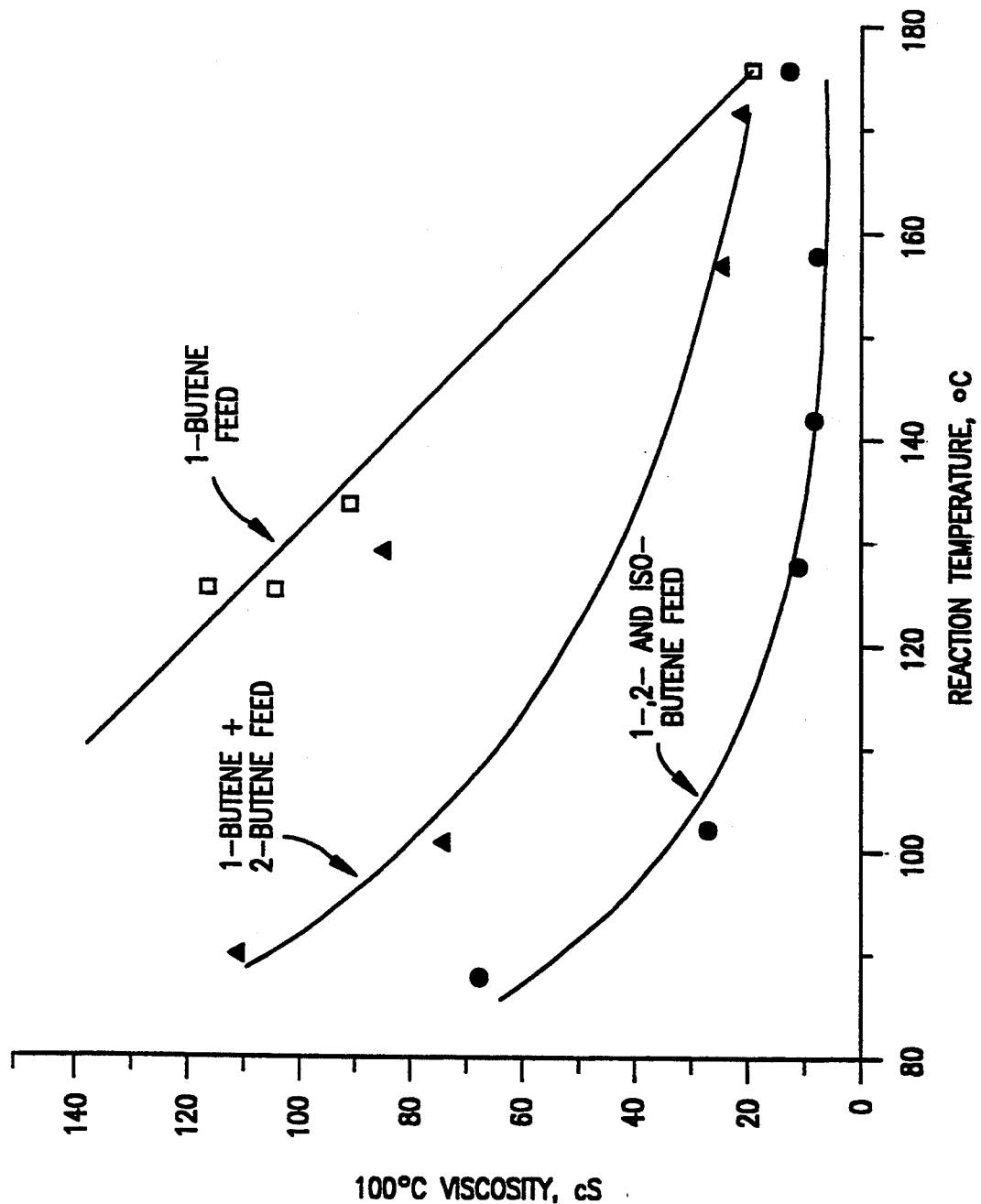

FIG. 3 shows the effect of reaction temperature on the viscosity of the oligomer product, using a mixed butene feed compared with a pure 1-butene feed. FIG. 3 shows that the product viscosity is lower from both mixed butene streams than from pure 1-butene feed at the same reaction temperature, at constant product VI (FIG. 4). Thus, the oligomerization of the 1-butene in the presence of the less reactive iso-butene and 2-butene favors the process configuration in which the oligomerization takes place before the etherification. However, since the less reactive internal olefins still exert an influence on the oligomerization, etherification first, to remove the iso-butene but leaving the 2-butene in the etherification effluent will still represent a favorable configuration.

We claim:

1. An integrated process for the production of lower alkyl tertiary alkyl ether and a higher molecular weight olefin oligomer from lower alkanol and $C_4+$ olefins containing alpha- olefins and iso-olefins, comprising:
   a) contacting a feed stream comprising the $C_4+$ olefins with reduced chromium oxide on silica support catalyst under oligomerization conditions in an oligomerization zone whereby 1-alkene component of the feedstream is selectively oligomerized to produce an effluent stream containing higher molecular weight olefin oligomer and unreacted $C_4+$ iso-olefins;
   b) separating and recovering the higher molecular weight olefin oligomer;
   c) passing the unreacted olefins and a lower alkanol feedstream to an etherification zone in which the unreacted $C_4+$ iso-olefins from step (a) are etherified with the alkanol in contact with acidic etherification catalyst under etherification conditions whereby an effluent stream is produced containing lower alkyl tertiary alkyl ether;
   d) separating and recovering the ether.

2. The process of claim 1 in which the lower alkanol comprises methanol and the lower alkyl tertiary alkyl ether comprises methyl tertiary butyl ether and/or methyl tertiary amyl ether.

3. The process of claim 1 in which the hydrocarbon feedstream comprises 1-butene, 2-butene, iso-butene and butane.

4. The process of claim 1 in which the $C_4+$ feedstream contains isoamylene.

5. The process of claim 1 in which the lower alkanol comprises between 2 and 100% stoichiometric excess of the lower alkanol.

6. The process of claim 1 in which the hydrocarbon feedstream comprises $C_4+$ olefins from an FCC unsaturated gas plant.

7. The process of claim 1 in which the oligomerization is carried out at a temperature of 90° to 250 °C.

8. The process of claim 1 in which the reduced chromium oxide catalyst has been treated by oxidation at a temperature of 200° to 900° C. in the presence of an oxidizing gas and then treatment with a reducing agent to reduce the catalyst to a lower valence state.

9. The process of claim 8 in which the reducing agent is carbon monoxide.

10. The process of claim 1 in which the higher molecular weight olefin oligomer is hydrogenated to produce saturated hydrocarbon.

* * * * *